United States Patent
Shindo et al.

(10) Patent No.: US 8,734,938 B2
(45) Date of Patent: May 27, 2014

(54) METHOD OF CUTTING OUT CHIPS FOR A PLURALITY OF SENSOR ELEMENTS FROM LAMINATED BODY, METHOD OF MANUFACTURING SENSOR ELEMENT, AND SENSOR ELEMENT

(75) Inventors: Hiroyuki Shindo, Kasugai (JP); Toyohiko Asai, Kasugai (JP)

(73) Assignees: NGK Insulators, Ltd., Nagoya (JP); NGK Printer Ceramics Co., Ltd., Komaki (JP)

( * ) Notice: Subject to any disclaimer, the term of this patent is extended or adjusted under 35 U.S.C. 154(b) by 562 days.

(21) Appl. No.: 12/406,171

(22) Filed: Mar. 18, 2009

(65) Prior Publication Data

US 2009/0239053 A1 Sep. 24, 2009

(30) Foreign Application Priority Data

Mar. 19, 2008 (JP) ................................. 2008-071258

(51) Int. Cl.
*G01N 27/407* (2006.01)

(52) U.S. Cl.
USPC .......................................... 428/221; 204/424

(58) Field of Classification Search
USPC ....................................................... 428/221
See application file for complete search history.

(56) References Cited

U.S. PATENT DOCUMENTS

| 6,027,622 | A | 2/2000 | Graser et al. |
| 6,620,302 | B1 | 9/2003 | Jach |
| 2004/0158971 | A1* | 8/2004 | Kawashima ................. 29/592.1 |
| 2005/0252770 | A1* | 11/2005 | Naito et al. .................... 204/424 |
| 2006/0024427 | A1 | 2/2006 | Clyde et al. |
| 2007/0000780 | A1* | 1/2007 | Oya et al. ....................... 204/424 |
| 2007/0007136 | A1 | 1/2007 | Awano et al. |
| 2007/0095662 | A1* | 5/2007 | Suzuki .......................... 204/424 |

FOREIGN PATENT DOCUMENTS

| EP | 0 309 360 | 3/1989 |
| EP | 0 678 740 A1 | 10/1995 |
| EP | 1 626 273 | 2/2006 |
| JP | 08-271476 A1 | 10/1996 |
| JP | 10-335170 | 12/1998 |

\* cited by examiner

*Primary Examiner* — Maria Veronica Ewald
*Assistant Examiner* — Laura Auer
(74) *Attorney, Agent, or Firm* — Burr & Brown, PLLC

(57) ABSTRACT

A sensor element is formed by cutting a laminated body and heating with the cutting taking place in a state where a difference in resistance on sides of a cutting component is as small as possible. That is, a uniform cutting is where resistance added to both sides of the cutting component is substantially the same. When uniform cutting cannot be performed, a nonuniform cutting in a state where resistance added to both sides of the cutting component is different is performed. Consequently, a surface perpendicular to a longitudinal direction of the sensor element is trapezoidal.

11 Claims, 13 Drawing Sheets

F I G. 9
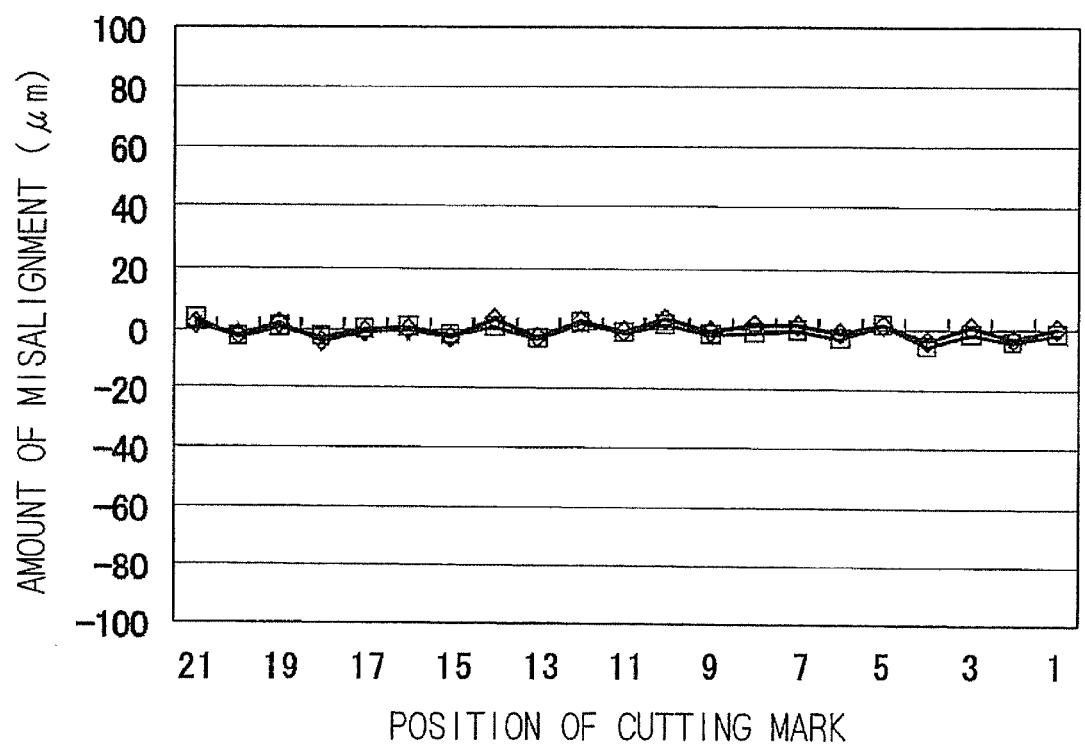

F I G . 1 1
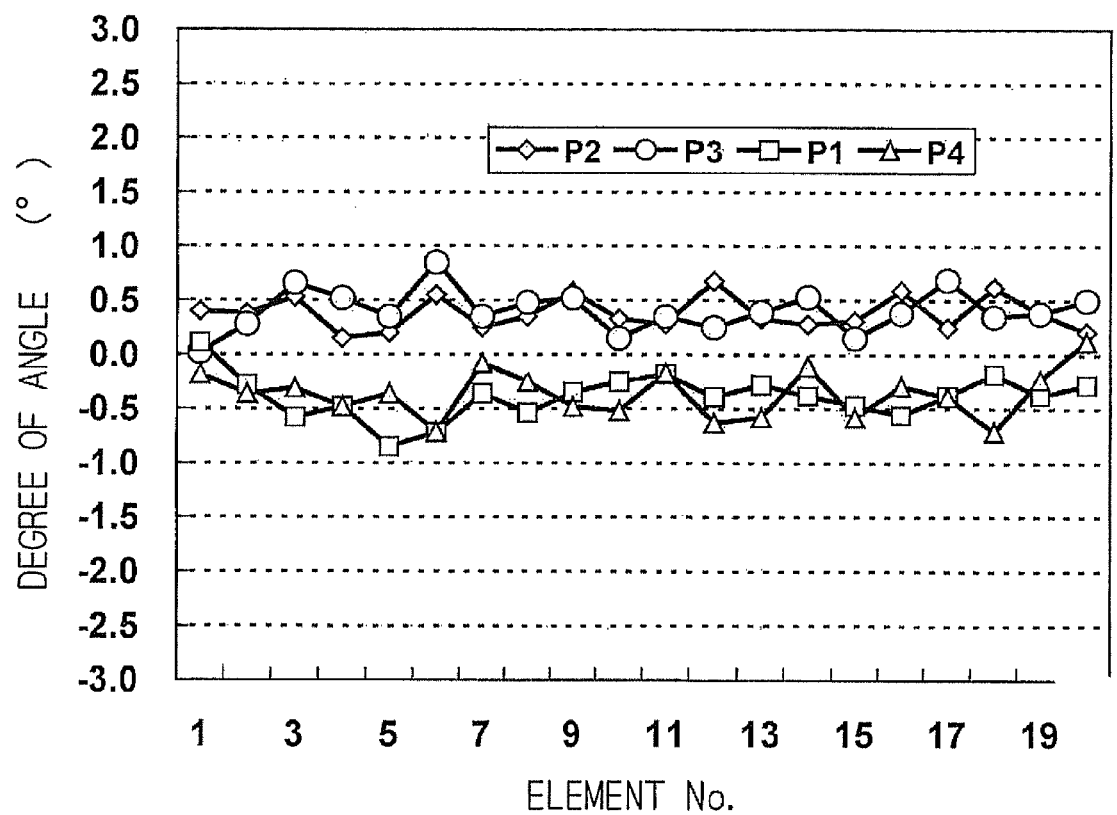

F I G . 1 3
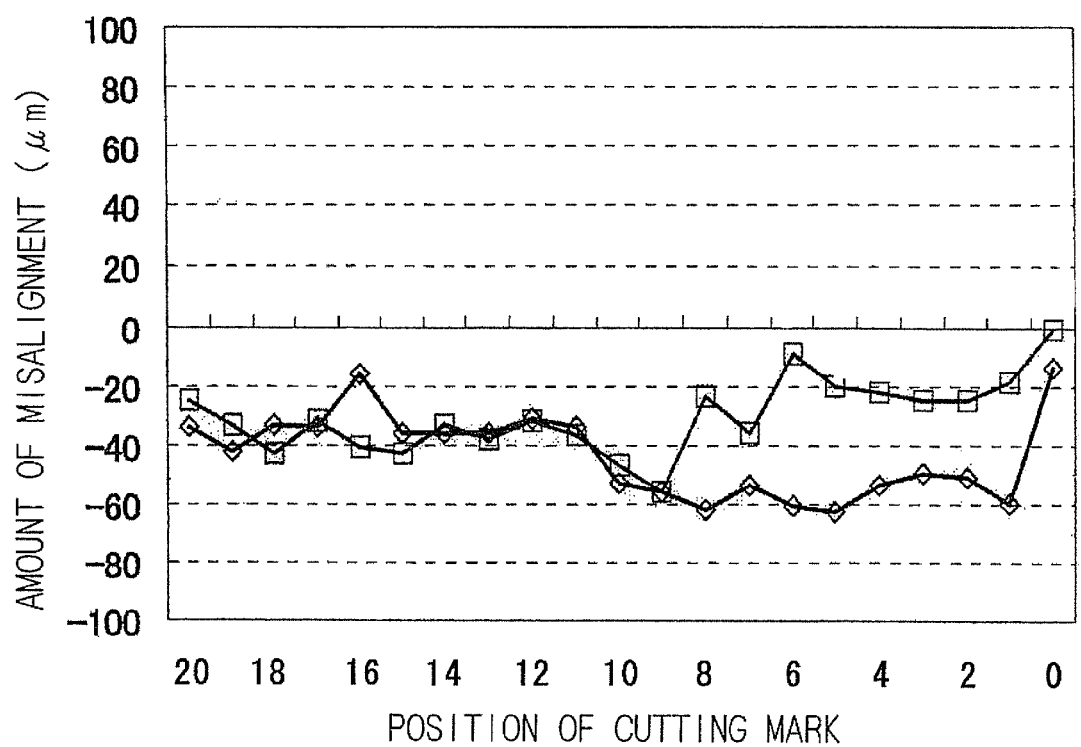

F I G. 1 4
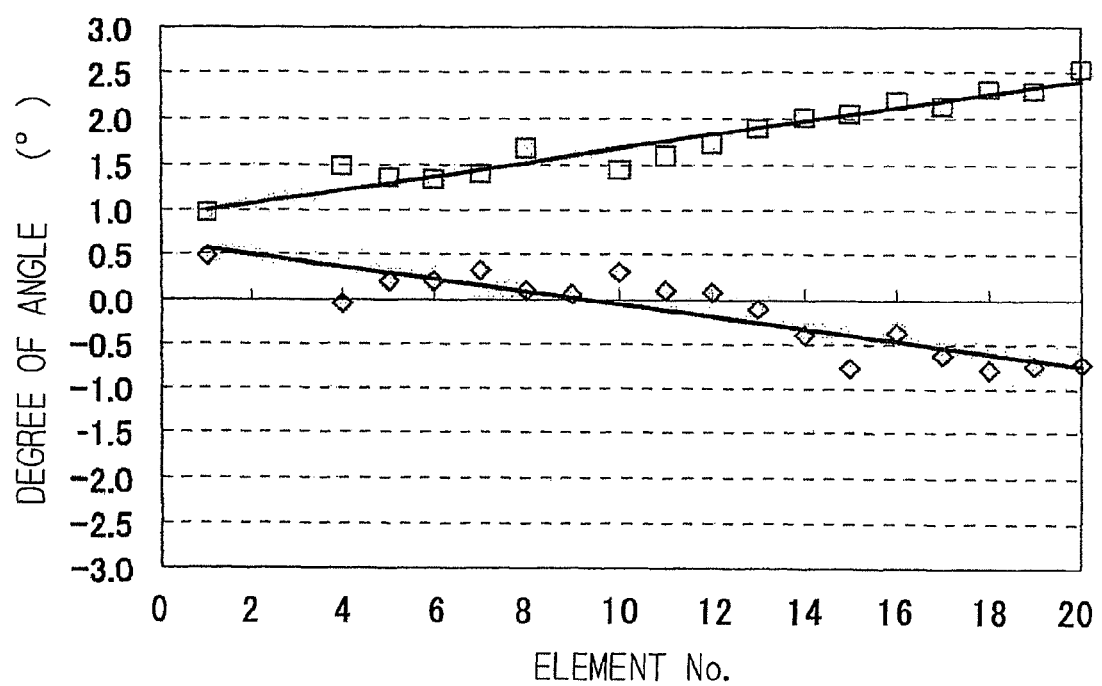

METHOD OF CUTTING OUT CHIPS FOR A PLURALITY OF SENSOR ELEMENTS FROM LAMINATED BODY, METHOD OF MANUFACTURING SENSOR ELEMENT, AND SENSOR ELEMENT

BACKGROUND OF THE INVENTION

1. Field of the Invention

The present invention relates to a sensor element manufactured by cutting out a laminated body formed by laminating ceramics green sheets, and a manufacturing method thereof.

2. Description of the Background Art

Conventionally, various measuring devices have been used for determining a concentration of a desired gas component in a measurement gas. A known device of measuring a NOx concentration in a measurement gas such as a combustion gas, for example, is a sensor having a Pt-containing electrode and a Rh-containing electrode formed on an oxygen ion conductive solid electrolyte, such as zirconia ($ZrO_2$) (see Japanese Patent Application Laid-Open No. 8-271476, for example).

A sensor element of a gas sensor as recited in Japanese Patent Application Laid-Open No. 8-271476 is manufactured as follows: forming circuit patterns (hereinafter also referred to as merely a "pattern") for a plurality of the sensor elements (e.g., several to several tens of the sensor elements) on each of a plurality of ceramics green sheets (hereinafter also referred to as merely a "green sheet") including zirconia which is an oxygen ion conductive solid electrolyte as a ceramics component, laminating those green sheets and integrating them to obtain a laminated body, then cutting the laminated body to obtain a plurality of cutting elements (chips), and burning those cutting elements. The manufactured sensor element is stored in a ceramics housing and held by a plate spring which also functions as a contact point to an external connection electrode provided on a surface of the sensor element.

In the gas sensor manufactured by the above described method, breaks and cracks are often generated in a side end portion of a longitudinal direction of the sensor element by an end portion of the sensor element making a contact with a housing, causing yield deterioration of manufacturing the gas sensor. Specifically, it has been a problem that such breaks and cracks are notably generated in a side where a heater of the sensor element is provided. The inventors of the present invention has confirmed that this is because that the sensor element does not have outline dimension in accordance with a predetermined design.

SUMMARY OF THE INVENTION

The present invention relates to a sensor element manufactured by cutting out a laminated body formed by laminating ceramics green sheets, and a manufacturing method thereof.

A method of cutting out a plurality of chips for sensor elements from a laminated body formed by laminating a plurality of ceramics green sheets according to the present invention includes the steps of (a) defining a cutting order of a plurality of cutting positions previously defined, the cutting order defined such that the cutting position is where a difference of resistance added to both side surfaces of a cutting edge of a cutting component is smallest at the time of cutting and (b) cutting the laminated body with the cutting component in accordance with the cutting order.

Thereby, the sensor element, in which breaks and cracks are difficult to be generated in a side end portion of a longitudinal direction, and the strength is more enhanced than before, can be obtained with excellent accuracy of dimension.

Preferably, in the step (a), the cutting order is defined such that when a cutting position capable of performing a uniform cutting exists among the plurality of cutting positions, the uniform cutting is performed at the cutting position by priority, and when the cutting position capable of performing the uniform cutting does not exist, nonuniform cutting is performed, the uniform cutting being performed in a state where resistance added to the both side surfaces of the cutting edge of the cutting component is substantially same, and the nonuniform cutting being performed in a state where resistance added to the both side surfaces of the cutting edge of the cutting component is different.

Thereby, the case of performing the nonuniform cutting, in which variations can be often generated in an outline shape of the sensor element, can be minimized. Accordingly, the sensor element, in which breaks and cracks are difficult to be generated in a side end portion of a longitudinal direction, can be obtained more reliably.

It is therefore an object of the present invention to provide a sensor element in which breaks and cracks are difficult to be generated, and a manufacturing method thereof.

These and other objects, features, aspects and advantages of the present invention will become more apparent from the following detailed description of the present invention when taken in conjunction with the accompanying drawings.

BRIEF DESCRIPTION OF THE DRAWINGS

FIG. 9 is a view showing the result of the amount of misalignment between a center position of a cutting mark for vertical cut and an intersection position of the corresponding actual cutting line at the time when cutting the laminated body.

FIG. 11 is a view showing the result of measuring the degrees of the angles P1 to P4 of twenty sensor elements obtained by burning twenty chips.

FIG. 13 is a view showing the result of the amount of misalignment in a horizontal direction between a center position of a cutting mark for vertical cut and a position of an intersection point of the corresponding actual cutting line, with respect to a chip according to a comparative example.

FIG. 14 is a view showing the result of measuring the degrees of the angles P2 and P3, with respect to the chip according to the comparative example obtained by cutting.

DETAILED DESCRIPTION OF THE INVENTION

<Gas Sensor>

Figure 1:
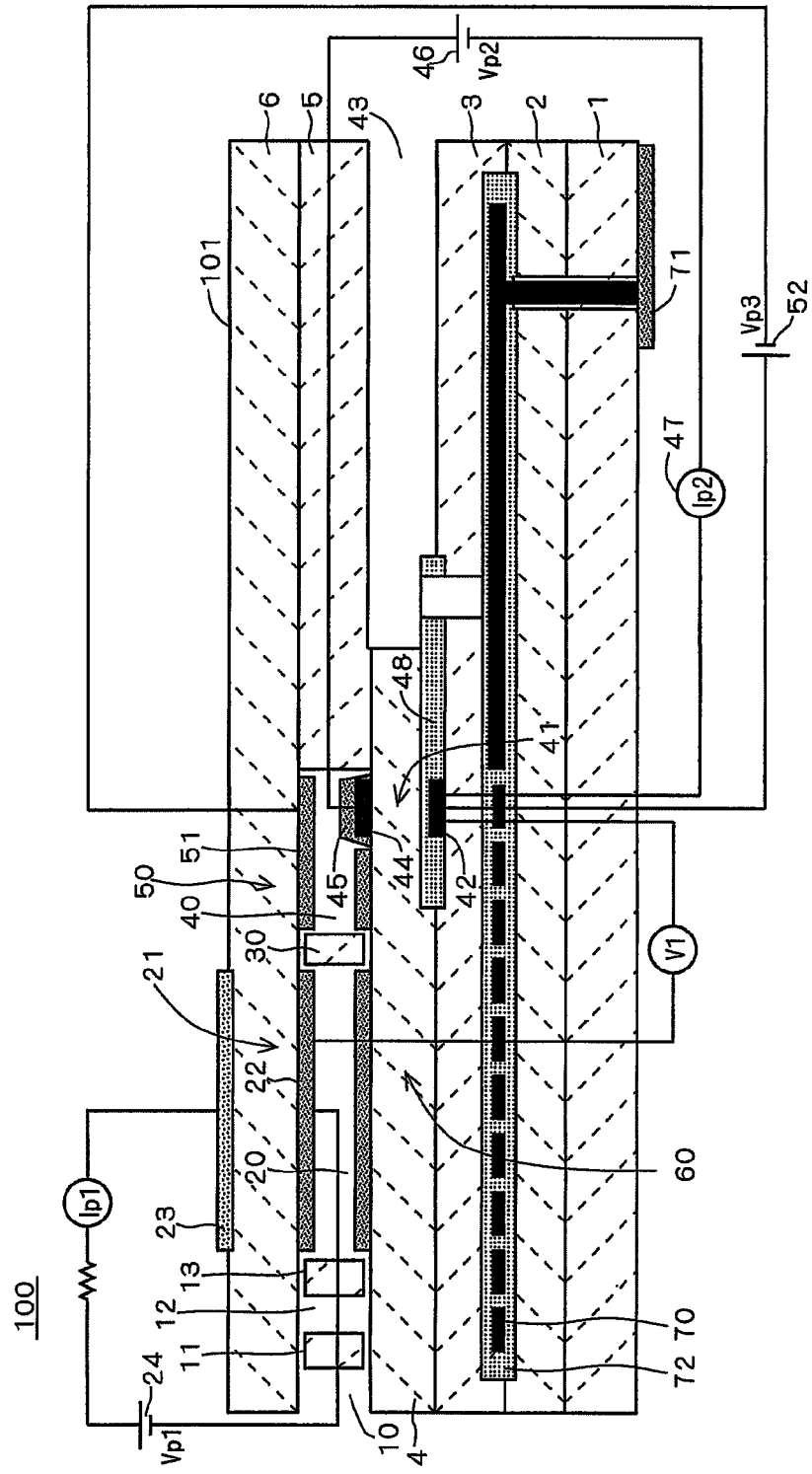
FIG. 1 is a cross-sectional diagram schematically showing a configuration of a gas sensor including a sensor element.

FIG. 1 is a cross-sectional diagram schematically showing a configuration of a gas sensor 100 including a sensor element 101 according to a present embodiment. The gas sensor 100 detects a predetermined gas component in a gas which is an object of measurement (a measurement gas), and further, measures a concentration thereof. The present embodiment will be described taking an example where the gas sensor 100 is a NOx sensor detecting nitrogen oxide (NOx) as an object component. The gas sensor 100 includes a sensor element 101 consisted of an oxygen ion conductive solid electrolyte such as zirconia ($ZrO_2$).

Specifically, the sensor element 101 includes a structure laminating six layers of a first substrate layer 1, a second substrate layer 2, a third substrate layer 3, a first solid electrolyte layer 4, a spacer layer 5, and a second solid electrolyte layer 6 in this order from a bottom seen in FIG. 1, each of the layers being consisted of an oxygen ion conductive solid electrolyte.

A gas inlet 10, a first diffusion control part 11, a buffer space 12, a second diffusion control part 13, a first internal space 20, a third diffusion control part 30 and a second internal space 40 are adjacently formed in this order in communication with one another between a lower surface of the second solid electrolyte layer 6 and an upper surface of the first solid electrolyte layer 4 at the end of the sensor element 101. The gas inlet 10, the buffer space 12, the first internal space 20 and the second internal space 40 are provided by hollowing out the spacer layer 5, which is a space with an upper portion sectioned by the lower surface of the second solid electrolyte layer 6, an lower portion sectioned by the upper surface of the first solid electrolyte layer 4, and a side portion sectioned by a side surface of the spacer layer 5. Each of the first diffusion control part 11, the second diffusion control part 13 and the third diffusion control part 30 is provided as two horizontally long slits (with an opening having a longitudinal direction in a direction perpendicular to FIG. 1). A part from the gas inlet 10 to the second internal space 40 is also referred to as a gas distribution part.

A reference gas inlet space 43 is provided between an upper surface of the third substrate layer 3 and a lower surface of the spacer layer 5 at a position which is far from the end than the gas distribution part is. The reference gas inlet space 43 is an internal space with an upper portion sectioned by the lower surface of the spacer layer 5, a lower portion sectioned by the upper surface of the third substrate layer 3, and a side portion sectioned by a side surface of the first solid electrolyte layer 4. For example, air is introduced to the reference gas inlet space 43 as a reference gas.

The gas inlet 10 is a portion which is open to an external space, and a measurement gas is brought into the sensor element 101 from the external space through the gas inlet 10.

The first diffusion control part 11 provides a predetermined diffusion resistance to the measurement gas brought into from the gas inlet 10.

The buffer space 12 is provided in order to counteract concentration fluctuation of the measurement gas caused by pressure fluctuation (pulsation of exhaust pressure if a measurement gas is an emission gas of automobiles) of the measurement gas in the external space.

The second diffusion control part 13 provides a predetermined diffusion resistance to the measurement gas brought into the second diffusion control part 13 from the buffer space 12.

The first internal space 20 is provided as a space for controlling oxygen partial pressure in the measurement gas introduced through the second diffusion control part 13. The oxygen partial pressure is controlled by operating a main pump cell 21.

The main pump cell 21 is an electrochemical pump cell composed of an inside pump electrode 22 provided on an almost whole surface in a part of the lower surface of the second solid electrolyte layer 6 facing the first internal space 20, an outside pump electrode 23 provided in a region corresponding to the inside pump electrode 22 on an upper surface of the second solid electrolyte layer 6 to be exposed outside, and a part of the second solid electrolyte layer 6 interposed between those electrodes. The inside pump electrode 22 and the outside pump electrode 23 are formed as porous cermet electrodes (e.g. cermet electrodes of Pt and $ZrO_2$ including Au by 1%) which are oblong in a plane view. Further, the inside pump electrode 22 is formed using material in which reduction ability to an NO component in the measurement gas is weakened, or material without reduction ability.

The main pump cell 21 is provided with a variable power source 24 outside the sensor element 101. The variable power source 24 applies a desired pump voltage Vp1 between the inside pump electrode 22 and the outside pump electrode 23 to flow pump current Ip1 in a positive direction or a negative direction between the outside pump electrode 23 and the inside pump electrode 22, allowing to pump out oxygen in the first internal space 20 to the external space or to pump in oxygen in the external space into the first internal space 20.

The third diffusion control part 30 provides a predetermined diffusion resistance to the measurement gas brought into the second internal space 40 from the first internal space 20.

The second internal space 40 is provided as a space for performing a process to measure concentration of nitrogen oxide (NOx) in the measurement gas introduced through the third diffusion control part 30.

A NOx concentration can be measured by operating a measuring pump cell 41. The measuring pump cell 41 is an electrochemical pump cell composed of a reference electrode 42 between the upper surface of the third substrate layer 3 and the first solid electrolyte layer 4, a measuring electrode 44 provided on the upper surface of the first solid electrolyte layer 4 facing the second internal space 40, spaced apart from the third diffusion control part 30, and the first solid electrolyte layer 4. Each of the reference electrode 42 and the measuring electrode 44 is a porous cermet electrode which is substantially oblong in a plane view. The reference electrode 42 is surrounded by an air induction layer 48 consisted of porous alumina and leading to a reference gas introduction space. The measuring electrode 44 is composed of metal obtained by resolving NOx which is a measurement gas component, and of porous cermet consisted of zirconia. Therefore, the measuring electrode 44 serves as a NOx reduction catalyst for resolving NOx in the atmosphere of the second internal space 40.

Moreover, the measuring electrode 44 is covered with a fourth diffusion control part 45. The fourth diffusion control part 45 is a film consisted of alumina, and functions to limit the amount of NOx flowing into the measuring electrode 44.

The measuring pump cell 41 is provided with a DC power source 46 applying a pump voltage Vp2 which is a fixed voltage between the measuring electrode 44 and the reference electrode 42 to resolve NOx. As a result, oxygen is generated in the atmosphere inside the second internal space 40, and then the oxygen is pumped out to the reference gas inlet space 43. A pump current Ip2 allowed to flow by the operation of the measuring pump cell 41 is detected by an ammeter 47.

Also, with respect to the measurement gas introduced through the third diffusion control part 30, oxygen partial pressure is previously controlled in the first internal space 20, and thereafter, the oxygen partial pressure is further controlled in the second internal space 40 by an auxiliary pump cell 50. Accordingly, the gas sensor 100 can perform the measurement of a NOx concentration with high precision.

The auxiliary pump cell 50 is an electrochemical pump cell composed of an auxiliary pump electrode 51 provided on substantially whole surface in a part of the lower surface of the second solid electrolyte layer 6 facing the second internal space 40, the second solid electrolyte layer 6, the spacer layer 5, the first solid electrolyte layer 4 and the reference electrode 42.

Similarly to the inside pump electrode 22, the auxiliary pump electrode 51 is formed using material in which reduction ability to an NO component in the measurement gas is weakened, or material without reduction ability.

The auxiliary pump cell 50 is provided with a DC power source 52 outside the sensor element 101. The DC power source 52 applies a fixed voltage Vp3 between the auxiliary pump electrode 51 and the reference electrode 42 to pump out oxygen in the atmosphere inside the second internal space 40 into the reference gas inlet space 43.

The sensor element 101 includes an oxygen partial pressure detecting sensor cell 60 which is an electrochemical pump cell composed of the inside pump electrode 22, the reference electrode 42, the second solid electrolyte layer 6, the spacer layer 5 and the first solid electrolyte layer 4.

The oxygen partial pressure detecting sensor cell 60 can detect oxygen partial pressure in the atmosphere of the first internal space 20 on the basis of a electromotive force V1 generated between the inside pump electrode 22 and the reference electrode 42 which is caused by the difference of oxygen concentration between the atmosphere of the first internal space 20 and a reference gas (air) of the reference gas inlet space 43. The detected oxygen partial pressure is used for feedback controlling the variable power source 24. Specifically, a pump voltage applied to the main pump cell 21 is controlled so as to set oxygen partial pressure in the atmosphere of the first internal space 20 at a predetermined value which is lower enough to be able to control oxygen partial pressure in the second internal space 40.

Moreover, the sensor element 101 includes a heater 70 formed to be interposed between the second substrate layer 2 and the third substrate layer 3 from above and below. The heater 70 generates heat by power feeding from outside through a heater electrode 71 provided on a lower surface of the first substrate layer 1. Heat generation by the heater 70 allows to enhance oxygen ion conductivity of solid electrolyte composing the sensor element 101. The heater 70 is buried over the whole area from the first internal space 20 to the second internal space 40 so that a predetermined area of the sensor element 101 is heated and kept warm at a predetermined temperature. A heater insulating layer 72 consisted of alumina or the like is formed on an upper surface and a lower surface of the heater 70 in order to obtain electronic insulation between the second substrate layer 2 and the third substrate layer 3 (hereinafter, the heater 70, the heater electrode 71 and the heater insulating layer 72 are also collectively referred to as a heater part).

In the gas sensor 100 having the above described structure, the measurement gas is provided with the measuring pump cell 41, with oxygen partial pressure constantly maintained at a fixed low value (value substantially not affecting the measurement of NOx) by operating the main pump cell 21 and the auxiliary pump cell 50. Accordingly, a pump current is to be substantially proportional to the reduced NOx concentration, the pump current flowing in the measuring pump cell 41 by pumping out oxygen generated by a reduction of NOx, thereby allowing to find out NOx concentration in the measurement gas.

<Outline Shape of Sensor Element>

Next, an outline shape (contour) of the sensor element in the gas sensor having the aforementioned configuration will be described.

Figure 2:
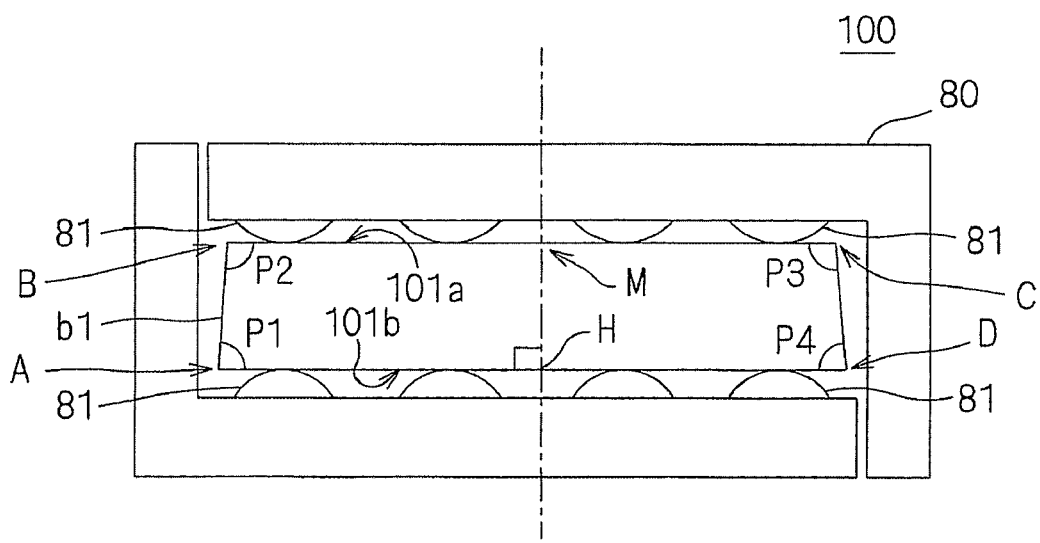
FIG. 2 is a diagram showing a state where the sensor element is stored in a housing.

FIG. 2 is a diagram showing a state where the sensor element 101 is stored in a ceramics housing 80 not shown in FIG. 1. The gas sensor 100 is used in the manner the sensor element 101 is stored in the housing 80. FIG. 2 shows the sensor element 101 seen in a direction from the right to the left of FIG. 1 (i.e., when seeing a surface perpendicular to the longitudinal direction). In FIG. 2, an upper surface of the sensor element 101 is a surface 101a (also referred to as a heater surface) of the first substrate layer on which the heater electrode 71 is provided, and a lower surface is a surface 101b (also referred to as a pump surface) of the second solid electrolyte layer 6 on which the outside pump electrode 23 is provided. The sensor element 101 is held in the housing 80 with the upper and lower surfaces 101a and 101b being biased with a plurality of plate springs 81 provided in the housing 80. Preferably, the plate springs 81 are provided so as to function also as contact points with electrodes such as the heater electrode 71.

As shown in FIG. 2, the outline shape of the sensor element 101 in a side surface view (cross-sectional view) is the quadrilateral ABCD in which the sides AD and BC (corresponding to the surfaces 101a and 101b) are substantially parallel to each other. Hereinafter, in the present specification, the outline shape of the sensor element will indicate a shape of the sensor element 101 seen in a manner as shown in FIG. 2.

To describe more in detail, in the present embodiment, the outline shape of the sensor element 101 is trapezoid in which the angles B and C at a side where the heater 70 is provided are not acute, and the angles A and D at the other side which are not obtuse. The typical outline shape is trapezoid in which the angles B and C are obtuse, and the angles A and D are acute.

In other words, when the middle point of the side BC is M, and the intersection of the perpendicular dropped from the middle point M to the side AD (perpendicular bisector of the side BC) and the side AD is H, the outline shape of the sensor element 101 satisfies the following equations.

$$AH \geq BM \quad (1), \text{ and}$$

$$DH \geq CM \quad (2), \text{ and}$$

$$AD > BC \quad (3).$$

Figure 3:
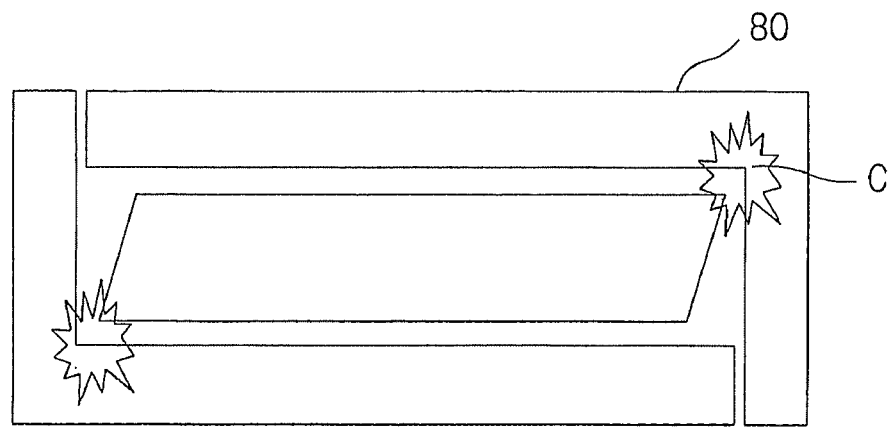
FIG. 3 is a diagram showing a state where a sensor element having the same inner structure of the sensor element according to a preferred embodiment, but having an acute angle C, is stored in a housing.

In contrast, FIG. 3 is a diagram showing a state where a sensor element having the same inner structure of the sensor element 101 according to the preferred embodiment, but having the acute angle C, is stored in the housing 80, and is shown in order to compare to FIG. 2. In use of the gas sensor, since the proximity of the heater 70 including the parts of the angles B and C is heated at a high temperature, the strength is reduced so that breaks and cracks are easily generated by making a contact with the housing 80 due to influence of vibration or the like. This is remarkable especially at each part of the angles B and C when the angle C is acute, or when the angle B is acute.

On the other hand, since the sensor element 101 according to the present embodiment is formed such that the angles B and C are not acute, as described above, such breaks and cracks are difficult to be generated. That is, according to the present embodiment, the configuration of the sensor element having the outline shape to satisfy the above equations (1) to (3) allows the gas sensor having the sensor element in which the strength is more enhanced than before.

When the degrees of the angles A, B, C and D are P1, P2, P3 and P4, respectively, as shown in FIG. 2, the sensor element 101 is preferably formed to satisfy the following equations.

$$0° \leq P2-90°, P3-90° \leq 1° \quad (4), \text{ and}$$

$$0° \leq 90°-P1, 90°-P4 \leq 1° \quad (5).$$

The relation of the left-hand side and the middle side in the equations (4) and (5) shows the aforementioned condition where the angles B and C are not acute, and the angles A and D at the other side are not obtuse. In addition, the relation of the middle side and the right-hand side in the equations (4) and (5) defines that misalignment of the respective angles from ninety degrees is less than or equal to 1 degree. In this case, breaks and cracks in the parts of the angles A and D are preferably suppressed.

<Manufacturing Process of Sensor Element>

Next, a process of manufacturing the sensor element 101 having the aforementioned outline shape will be described. According to the present embodiment, the sensor element 101 is manufactured by forming a laminated body consisted of green sheets including oxygen ion conductive solid electrolyte such as zirconia as a ceramics component, cutting and burning the laminated body.

Hereinafter, the case of manufacturing the sensor element 101 composed of six layers shown in FIG. 1 will be described as an example. In this case, six green sheets are prepared to correspond to the first substrate layer 1, the second substrate layer 2, the third substrate layer 3, the first solid electrolyte layer 4, the spacer layer 5 and the second solid electrolyte layer 6, respectively.

Figure 4:
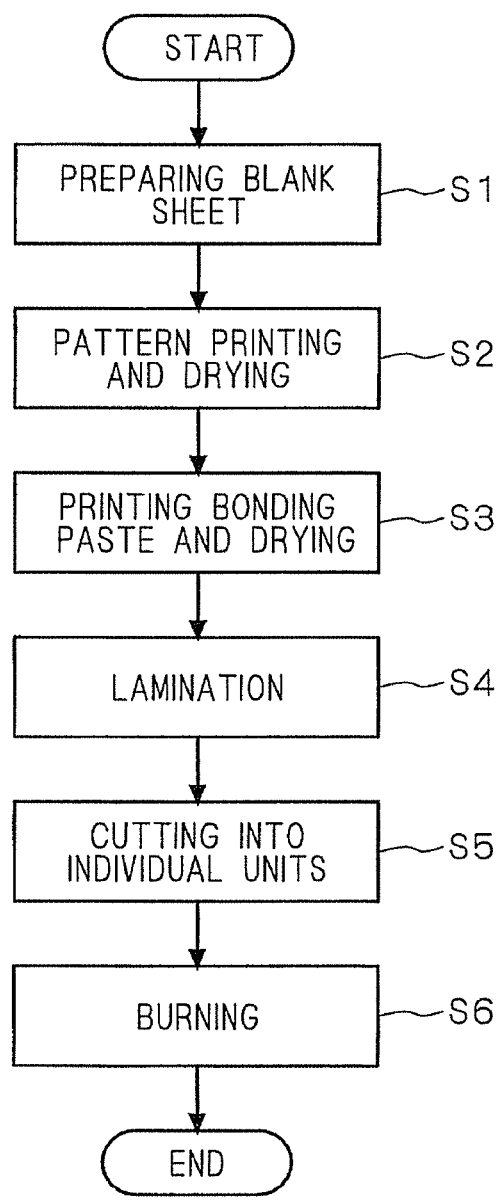
FIG. 4 is a flow of a process of manufacturing the sensor element.
Figure 5:
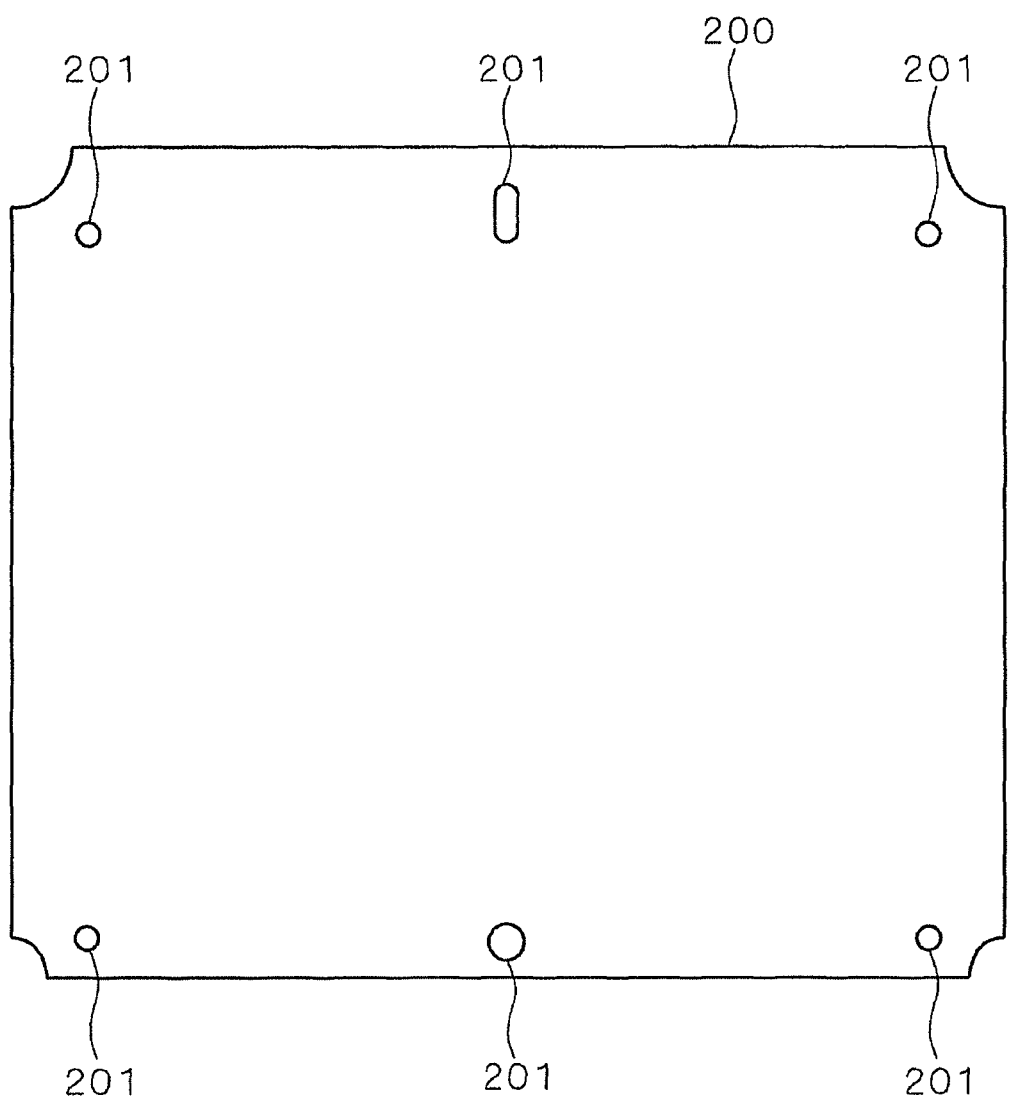
FIG. 5 is a diagram showing a blank sheet which is a green sheet on which a pattern is not formed.

FIG. 4 illustrates a flow of a process in manufacturing the sensor element 101. Also, FIG. 5 illustrates a blank sheet 200 which is a green sheet on which a pattern is not formed. When manufacturing the sensor element 101, firstly, blank sheets 200 are prepared (a step S1). When manufacturing the sensor element 101 composed of six layers, six blank sheets 200 are prepared to correspond to each layer of the sensor element 101. The blank sheets 200 are provided with a plurality of sheet holes 201 used for positioning in printing or in laminating. These sheet holes 201 are previously provided on the blank sheets 200 before forming a pattern by the punching process with a punching machine or the like. In the case of a green sheet which corresponds to a layer composing an inner space, a penetrating portion corresponding to the inner space is previously provided by the similar punching process. It should be noted that thickness of each blank sheet 200 corresponding to each layer of the sensor element 101 is not necessarily same with each other.

After preparing the blank sheets 200, the pattern printing and drying process are performed on each of the blank sheets 200 (a step S2). A publicly known screen printing process is available for printing a pattern and an adhesive. Also, a publicly known drying process is available for the drying process after printing. With respect to the first substrate layer 1, a cutting mark to be a reference of a cutting position when cutting the laminated body in the subsequent process is also printed thereon. After the pattern printing, the printing and drying process of a bonding paste are performed for laminating and bonding each green sheet corresponding to each layer (a step S3).

Subsequently, the crimping process is performed for obtaining a single laminated body by laminating green sheets, on which the adhesive is applied, in a predetermined order, and crimping them with a predetermined temperature and a pressure condition (a step S4). More specifically, the green sheets to be the objects of lamination are held onto a predetermined lamination jig not shown by positioning in accordance with the sheet holes 201, and the green sheets are heated and pressurized together with the lamination jig by a lamination machine such as a known oil-hydraulic press machine. Pressure, temperature and period for heating and pressurizing depend on which laminating machine is used, but suitable conditions may be set for achieving a preferable lamination.

After obtaining the laminated body as described above, subsequently, several parts of the laminated body are cut into individual units of the sensor element 101 (referred to as a chip) (a step S5). This method of cutting the laminated body is distinctive in obtaining the outline shape of the aforementioned sensor element. Therefore, details thereof will be described later.

The sensor element 101 having the aforementioned outline shape is generated by burning the cut-out chip under a predetermined condition (a step S6).

The sensor element 101 obtained in accordance with the above is stored in a predetermined housing, and assembled into a main body (not shown) of the gas sensor 100.

<Cutting Device>

Figure 6:
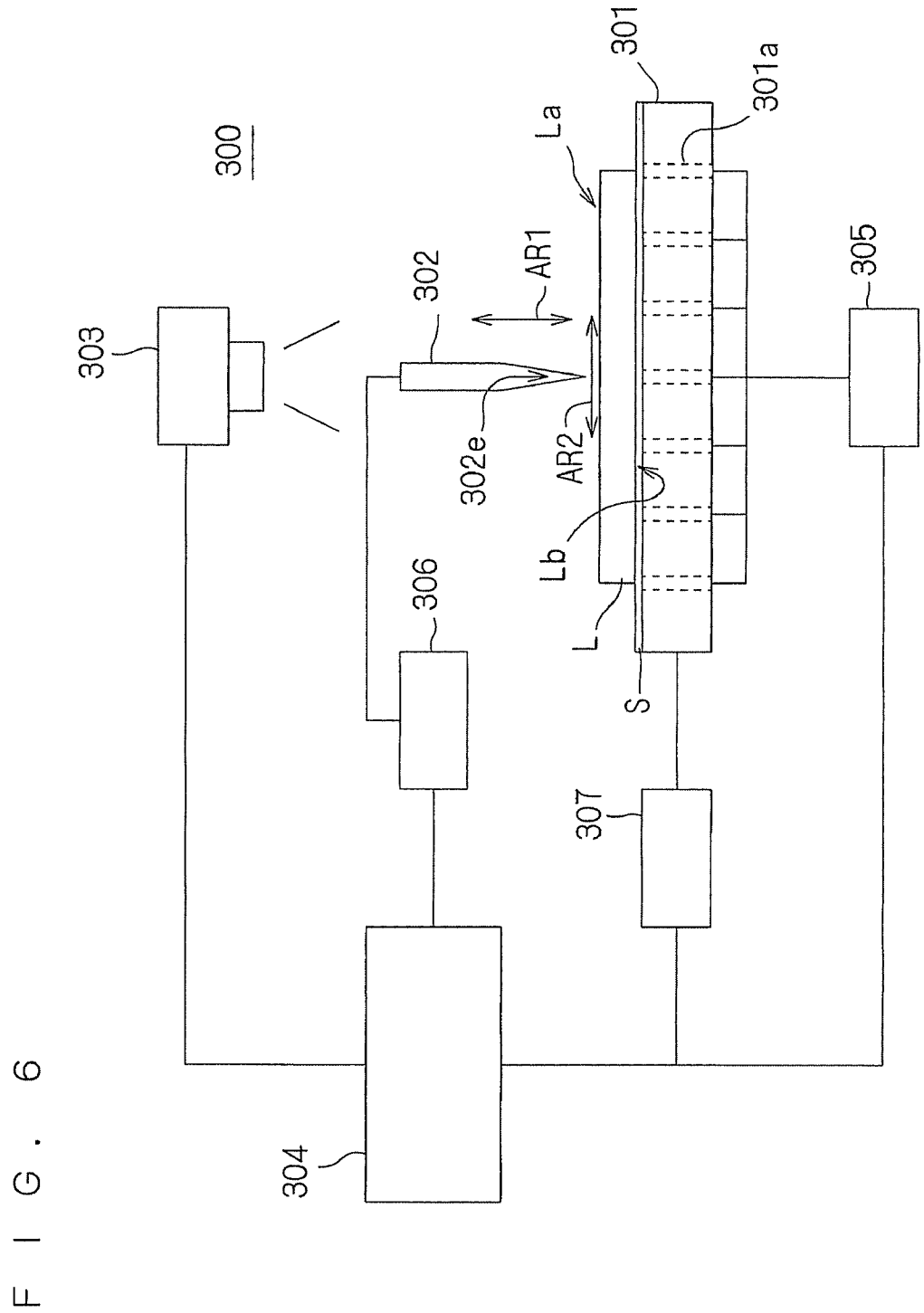
FIG. 6 is a diagram schematically showing a configuration of a cutting device as an example of devices used for cutting a laminated body.

The method of cutting the laminated body will be specifically described hereinafter. First, the cutting device will be described as an example of devices used for cutting the laminated body. FIG. 6 is a diagram schematically showing a configuration of a cutting device 300 as an example of devices used for cutting the laminated body. The method of cutting the laminated body described below is basically possible to be implemented in other cutting devices other than the cutting device 300.

The cutting device 300 includes a stage 301 for placing a laminated body L to be an object of cutting, a cutting knife 302 which is a member of performing the cutting at a predetermined cutting position, a imaging means 303 for talking an image of the laminated body L placed on the stage 301 and a controlling means 304 for controlling the operation of each part of the device.

The numbers of suction holes 301a are provided on the stage 301, and a suction means 305 can give negative pressure on the suction holes 301a. When cutting a predetermined position of the laminated body L by the cutting device 300, an adhesive sheet S is applied on a cutting-end surface which is an opposite surface of a cutting-start surface on which a cutting mark is provided (surface with which the cutting knife 302 makes a contact at the beginning of the cutting), and then, the laminated body L is placed on the stage 301, being attached and fixed thereon by performing suction with the suction means 305. As shown in FIG. 6, a surface La is to be the cutting-start surface and a surface Lb is to be the cutting-end surface in the present embodiment. The surface La is a surface to be a heater surface, and the surface Lb is a surface to be a pump surface.

The cutting knife 302 may be appropriately selected in accordance with material and solidness of the laminated body L to be an object of cutting. However, when the laminated body is formed by laminating green sheets mainly including zirconia as a ceramics component, it is preferable to use a cemented-carbide-step blade.

The cutting knife 302 is formed with its upper portion being held by a holding means not shown to be movable in a vertical direction shown by an arrow AR1 and in a horizontal direction shown by an arrow AR2 by a knife driving means 306. In contrast, the stage 301 is formed to be translatable and rotatable in a horizontal surface by a stage driving means 307, or may be formed to be further movable in a vertical direction.

On the other hand, the imaging means 303 is provided to observe the cutting-start surface (the surface La in FIG. 6) of the laminated body L placed on the stage 301.

In the cutting device 300, the cutting position by the cutting knife 302 is determined by the controlling means 304 recognizing the cutting mark provided on the surface La on the basis of an image of the imaging means 303, and specifying its position. The knife driving means 306 and the stage driving means 307 control (align) the positions of the cutting knife 302 and the stage 301 in response to a control signal from the controlling means 304 so as to perform the cutting at the determined cutting position. Subsequently, the cutting knife 302 descends to a vertical direction at the cutting position determined in response to the control signal of the controlling means 304, allowing to implement the cutting at the determined cutting position.

<Cutting Mark>

Figure 7:
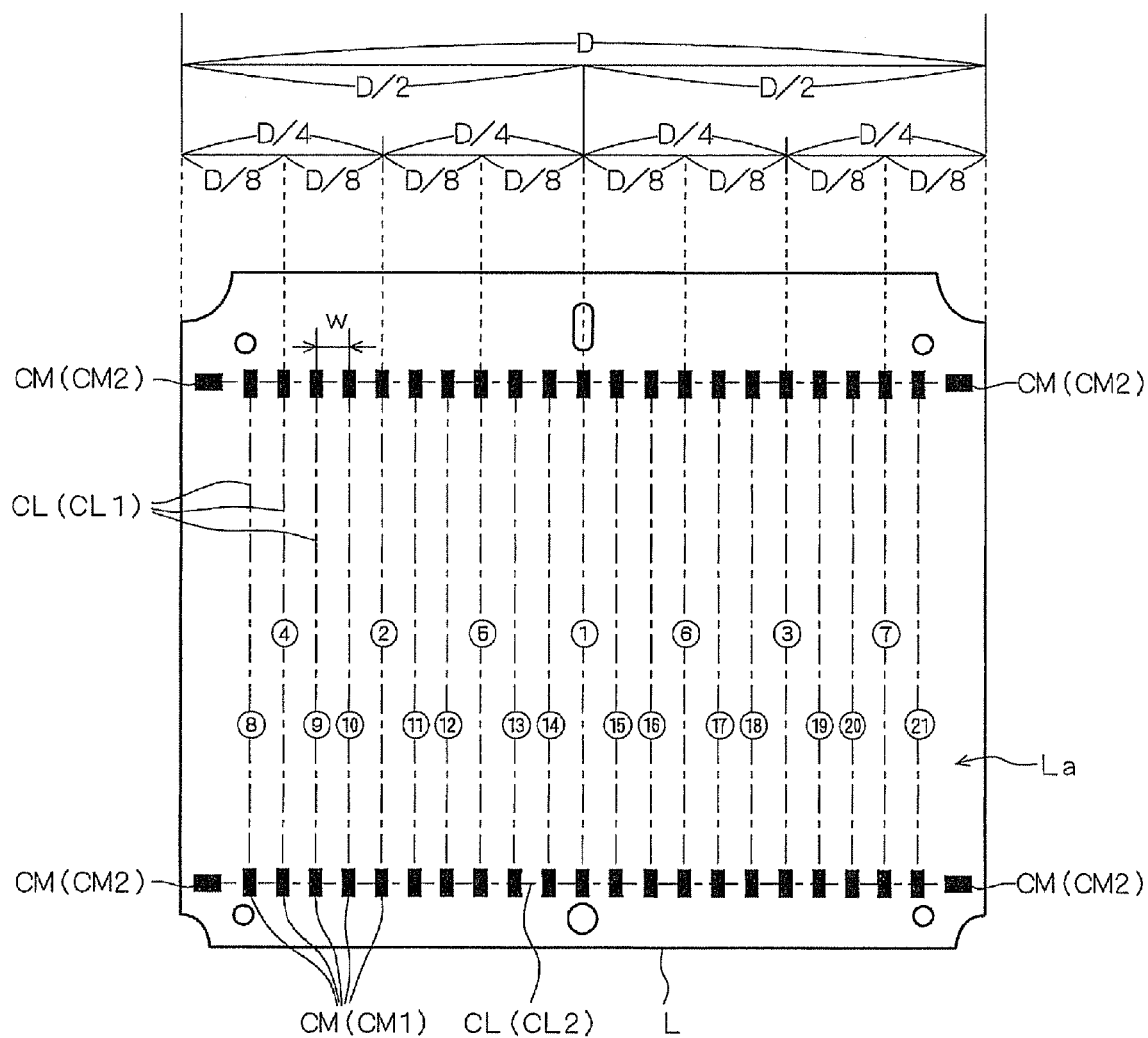
FIG. 7 is a diagram showing a cutting-start surface of the laminated body.

FIG. 7 is a diagram showing the surface La which is a cutting-start surface of the laminated body L. The size of the laminated body L in a transverse direction seen in FIG. 7 is made as D, and the width of a single chip (size in a transverse direction seen in FIG. 7) is made as w. A plurality of cutting marks CM in a rectangle shape are formed on the surface La in a printing process described above. FIG. 7 illustrates the case of forming the cutting marks CM so as to obtain twenty long chips along the transverse direction of FIG. 7 from a single laminated body L. It should be noted that printing patterns other than the cutting marks CM are omitted for simplifying in FIG. 7. Actually, a pattern of such as an electrode functioning as a connection terminal is printed.

The cutting marks CM are roughly classified into vertical cutting marks CM1 and horizontal cutting marks CM2. The vertical cutting marks CM1 are formed with two of them, above and below as seen in FIG. 7, as a pair. In the surface La shown in FIG. 7, twenty one pairs of the vertical cutting marks CM1 totaling forty two are provided to obtain twenty chips.

When cutting to be parallel to a vertical direction in FIG. 7 (referred to as merely a vertical cutting), each time of performing the cutting, the position of a pair of two vertical cutting marks CM1 is specified on the basis of the image by the imaging means 303. Then, on the basis of the above result, alignment may be appropriately performed by adjusting the position of the cutting knife 302 with the knife driving means 306, or adjusting the horizontal position or the position in the horizontal surface of the stage 301 with the stage driving means 307, and thereafter, the cutting knife 302 cuts between two vertical cutting marks CM1.

In FIG. 7, while cutting lines CL are shown in chain line, the cutting lines CL are drawn for description, and not necessarily formed on the actual surface La.

The horizontal cutting mark CM2 are formed with two of them, right and left as seen in FIG. 7, as a pair. Two pairs of the horizontal cutting marks CM2 totaling four are provided. The horizontal cutting marks CM2 are referred to after a vertical cutting, when cutting end portions above and below of each chip at the cutting line CL (CL2) perpendicular to the cutting line CL1 for a vertical cutting (referred to as merely a horizontal cutting). A horizontal cutting is performed after the stage 301 is rotated ninety degrees in the horizontal surface from the position of the vertical cutting.

As such, in the method according to the preferred embodiment, alignment of the cutting positions is performed by specifying the positions of the cutting marks each time of cutting the laminated body, allowing to suppress misalignment of the cutting positions in the horizontal surface caused by deformation due to contraction of a green sheet, thereby ensuring accuracy of dimension of the sensor element.

Instead of providing the cutting marks CM corresponding to all the cutting lines as described above, it is considered to previously specify the position of the cutting lines only at most external sides with the cutting marks or the like, and to determine the cutting positions such that the internal region is divided equally in accordance with the number of chips which are cut out. In this case, however, misalignment between the intended cutting position and the actual cutting position is easily generated due to contraction of a green sheet, therefore, it is not preferable in view of ensuring accuracy of dimension.

<Cutting Order>

Next, the cutting order when cutting the laminated body L, specifically the vertical cutting for sequentially cutting at several points will be described in detail. In the present embodiment, the sensor element is formed to satisfy the equations (1) to (3) and further the equations (4) to (5) by managing this cutting order.

Figure 8A:
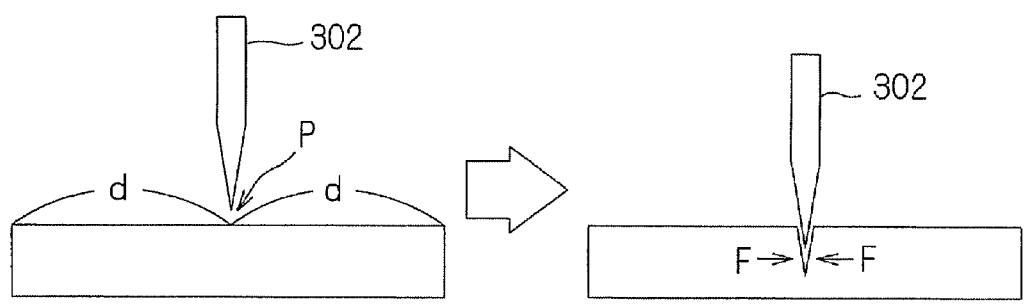
FIGS. 8A and 8B are diagrams showing a relation between a cutting position and resistive force added from a cutting surface at the time when cutting the laminated body with a cutting knife.
Figure 8B:
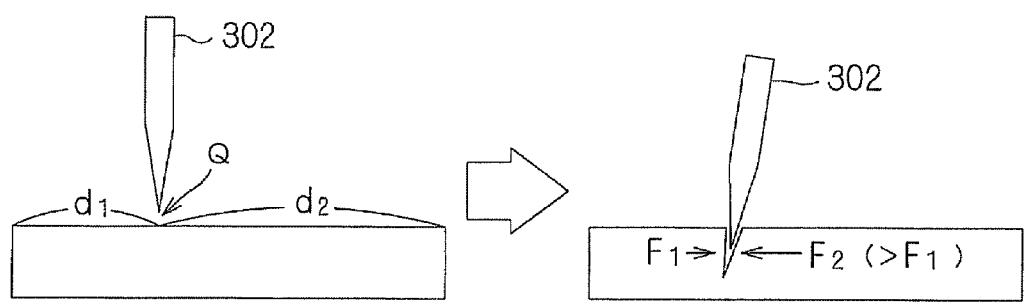

FIGS. 8A and 8B are diagrams showing a relation between a cutting position and resistive force added from a cutting surface (repulsive force against cutting) at the time when cutting the laminated body L with the cutting knife 302. When cutting the laminated body L with the cutting knife 302, resistive force from the cutting surface of the laminated body L (repulsive force from the laminated body L against cutting) is added to both side surfaces of a cutting edge 302e of the cutting knife 302. This resistive force is derived from elasticity of the laminated body L, and is the force which acts more greater as thickness of a continuous part of the laminated body L in an in-plane direction of the laminated body L substantially perpendicular to the cutting direction (direction to thickness of the laminated body L), that is, a distance between the cutting position and the end portion of the laminated body L (or distance between the cutting position and the cutting surface which is already cut) is getting greater. That is, the magnitude relation of resistive force acting on the both side surfaces of the cutting edge 302e of the cutting knife 302 is determined on the basis of thickness of the continuous part of the laminated body in a direction of both sides of the cutting position.

For instance, as shown in FIG. 8A, when the cutting position is located at a position having an equal distance d from the end portions of right and left, the resistive force F having substantially equal magnitude is put on the both sides of the cutting knife 302 when cutting so that the cutting edge 302e of the cutting knife 302 descends straight downward in a vertical direction, resulting in obtaining a symmetrical cutting surface. The cutting in the above manner is referred to as an "uniform cutting".

In contrast, as shown in FIG. 8B, when the cutting position is located at a position having a distance d2 from the right end portion being larger than a distance d1 from the left end portion, the resistive force F2 added to the right side surface of the cutting knife 302 becomes larger than the resistive force F1 added to the left side surface when cutting. Since the cutting edge 302e of the cutting knife 302 is not constituted to descend exactly downward in a vertical direction by being guided with some means or the like, the cutting edge 302e is going to descend away toward the left side added smaller resistive force. The cutting in the above manner is referred to as a "nonuniform cutting". In the nonuniform cutting, the shape of the cutting surfaces of right and left differ, depending on the extent of resistance added to the right and left sides of the cutting edge 302e. In FIG. 8B, the inclination of the cutting knife 302 is shown with exaggeration for being easily understandable. In reality, the inclination of at most a few degrees can be generated.

From the above, the more frequently the nonuniform cutting is performed in manufacturing the sensor element 101, the more often the variation of the outline shape of the sensor element 101 is generated.

Accordingly, in the present embodiment, when performing the vertical cutting at several points, the uniform cutting is performed by priority, and the nonuniform cutting is performed only when the uniform cutting cannot be performed. Even when the nonunifrom cutting is performed, the cutting in a state where difference of the resistive force added to the both side surfaces of the cutting edge 302e of the cutting knife 302 is small is performed by priority. In other words, the cutting in a state where difference of the resistance generated at the both side surfaces of the cutting edge 302e of the cutting knife 302 is small is performed by priority. The size of the sensor element 101 (size of a chip), the size of a green sheet (or size of a peripheral region becoming unnecessary after division) and the number of chips which are cut out from a single laminated body L, are previously defined to preferably perform the cutting in the above manner. When performing the cutting with the cutting device 300, being given the above information, the controlling means 304 may carry out an operation on the basis of the image result of the imaging means 303 to define the cutting order as described above, or being given the cutting order defined as described above as information, the controlling means 304 may perform only a process for aligning each cutting position.

For instance, in the case of the laminated body L shown in FIG. 7, the cutting (vertical cutting) is performed at each cutting line CL1 in the order shown by the circled number in FIG. 7. The position of the cutting line CL1 shown by the circled number 1 is referred to as a "cutting position [1]" and the like, hereinafter.

First, the cutting is performed at the cutting position [1] to divide the size D in a transverse direction of the entire surface La equally. This cutting is the uniform cutting so that the shape of the cutting surface is symmetrical.

Next, two portions (the portions of the size D/2 in a transverse direction) which are divided into two by the cutting at the cutting position [1] are further divided equally at the cutting positions [2] and [3]. At this time, the cutting positions [2] and [3] are not symmetrical to right and left when seeing the entire surface La. However, since the cutting at the cutting positions [2] and [3] is performed after the cutting at the cutting position [1], in the case of the cutting position [2], for example, the right half region does not affect the resistive force added to the cutting knife 302. Also, when determining if the cutting is to be the uniform cutting or the nonuniform cutting, it is thickness of the continuous part of the laminated body that is to be considered. Thus, if it is used as a chip or not is irrelevant. Therefore, the peripheral parts which are not to be cut out as a chip are to become objects of this determination. In view of the above, the cutting at the cutting positions [2] and [3] is the uniform cutting, and the shape of the cutting surface is to be symmetrical to right and left. The cutting order at the cutting positions [2] and [3] may be exchanged.

After finishing the cutting at the cutting position [3], the total of four portions (the portions of the size D/4 in a transverse direction) which are divided equally by the cutting at the cutting positions [2] and [3] are further divided equally at the cutting positions [4], [5], [6] and [7]. The cutting at these four cutting positions are also the uniform cutting, and the shape of the cutting surface is to be symmetrical to right and left. The cutting order at the cutting positions [4], [5], [6] and [7] may be exchanged.

After finishing the cutting at the cutting position [7], the cutting line CL1 capable of performing the uniform cutting does not exist at this point. Therefore, next cutting will be the nonuniform cutting. In the case shown in FIG. 7, the position where the difference of the distance between the cutting position and the end portion of the laminated body L (between the cutting position and the cutting surface which is already cut) is the width w of a single chip is the one capable of performing the nonuniform cutting in a state where difference of the resistive force added to the both side surfaces of the cutting edge 302e of the cutting knife 302 is the smallest. Accordingly, the cutting line to satisfy the above condition is to be the next candidate of the cutting, and all the cutting positions [8] to [21] in the laminated body L shown in FIG. 7 are to satisfy this condition. This is because the laminated body L is already cut at the intervals corresponding to three chips, by this point.

Accordingly, as shown in FIG. 7, the cutting can be performed in the order of the cutting positions [8] to [21]. The cutting at the cutting position [9] divides the part of three chips into the part of one chip and the part of two chips so that the next cutting at the cutting position [10] is to divide the part of two chips equally. That is, the cutting at the cutting position [10] is to be the uniform cutting again. Thereafter, the cutting at the cutting positions [11] to [21] is similarly performed by repeating the nonuniform cutting and the uniform cutting in turn.

As a result, in the case of the laminated body L shown in FIG. 7, the nonuniform cutting is performed only at eight positions of the cutting positions [8], [9], [11], [13], [15], [17], [19] and [21] out of the twenty one cutting positions for the vertical cutting, and the uniform cutting is performed at other thirteen positions. Moreover, each of the nonuniform cutting is performed to divide the part consisted of one chip and two chips so that the difference of the resistance at both side surfaces of the cutting edge 302e of the cutting knife 302 at that time is considered to be relatively small, and is believed that the impact on the outline shape of the sensor element is relatively small. When exchanging the cutting order at the cutting positions [8] to [21], which cutting positions is to be the nonuniform cutting or is to be the uniform cutting is exchanged accordingly, but the number of the nonuniform cutting and the uniform cutting is same.

If the cutting is performed in the order from either end of the right and left with respect to the twenty one cutting positions, all the cuttings are to be the nonuniform cuttings. Comparing to this, the case of performing the uniform cutting increases when performing the cutting in the cutting order of the present preferred embodiment. That is, it is preferable to perform the cutting in the cutting order of the present preferred embodiment in obtaining the sensor element with high accuracy of dimension more reliably. The inventors of the present invention have confirmed that the outline shape of a chip obtained by performing the cutting in the above cutting order is to be trapezoid satisfying the equation (1) or the equation (5) which is primarily a condition of the sensor element after burning, and this outline shape can be maintained after burning (See example below).

As described above, according to the present embodiment, the sensor element in which breaks and cracks are difficult to be generated in a side end portion of a longitudinal direction, can be obtained with high accuracy of dimension.

The positions of the cutting marks shown in FIG. 7 are only examples, thus, it is needless to say that the uniform cutting may be actually performed subsequently after the cutting at the cutting position [7] is finished, depending on the relation of the number of elements, the element size, or the size of unnecessary portion.

Inventive Example

The sensor element was manufactured by the steps S1 to S6 according to the aforementioned preferred embodiment. Twenty sensor elements were to be obtained from a single laminated body by forming the cutting marks CM as shown in FIG. 7. The cutting of chips were performed such that the cutting in a state where difference of resistance generated in both side surfaces of the cutting edge 302e of the cutting knife 302 was small was performed by priority, more specifically, the cutting of elements were performed by aligning the cutting positions by specifying the positions of the cutting marks in the cutting order shown in FIG. 7, and each time of cutting the laminated body.

FIG. 9 is a view showing the result of the amount of misalignment (amount of misalignment in a horizontal direction) between the center position of the vertical cutting mark CM1 having twenty one pairs totaling forty two and the intersection position of the corresponding actual cutting line CL1 and the cutting line CL2 at the time when cutting the laminated body L. The triangles show the result of the cutting marks CM1 at the upper side seen in FIG. 7, and the squares show the result of the cutting marks CM1 at the lower side seen in FIG. 7. The average value of the amount of misalignment in the horizontal direction is 0.6 μm, and the standard deviation is 2.6 μm. It has been thus confirmed that the cutting was performed almost accurately at the positions specified as the cutting positions.

Figure 10:
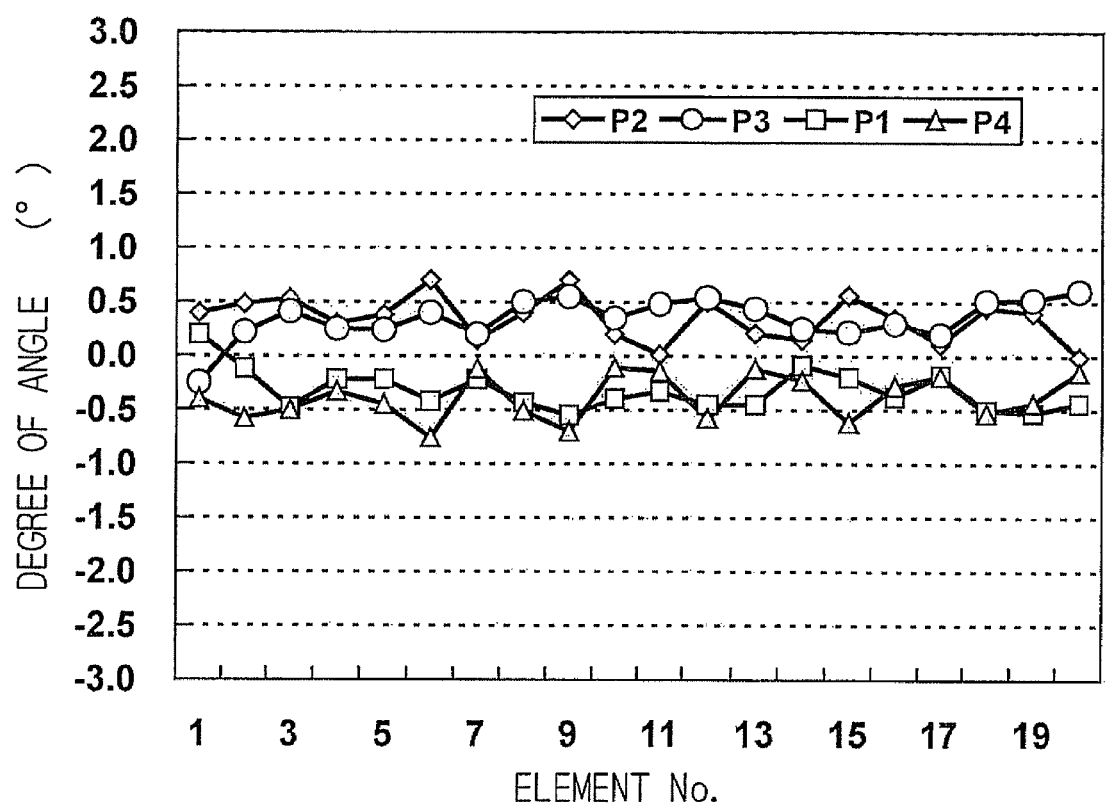
FIG. 10 is a view showing the result of measuring the degrees of the angles P1 to P4 of twenty chips obtained by cutting.

FIG. 10 is a view showing the result of measuring the degrees of the angles P1 to P4 of twenty chips obtained by the cutting. In FIG. 10, misalignment of the degrees of the respective angles from ninety degrees is plotted. The result shown in FIG. 10 shows most chips have the degrees of the angles P1 and P4 which are acute angles smaller than ninety degrees within a range of one degree, and the degrees of the angles P2 and P3 which are obtuse angles larger than ninety degrees within a range of one degree. It has been thus confirmed that the outline shape of the chip is trapezoid satisfying the equations (1) to (3).

Figure 12:
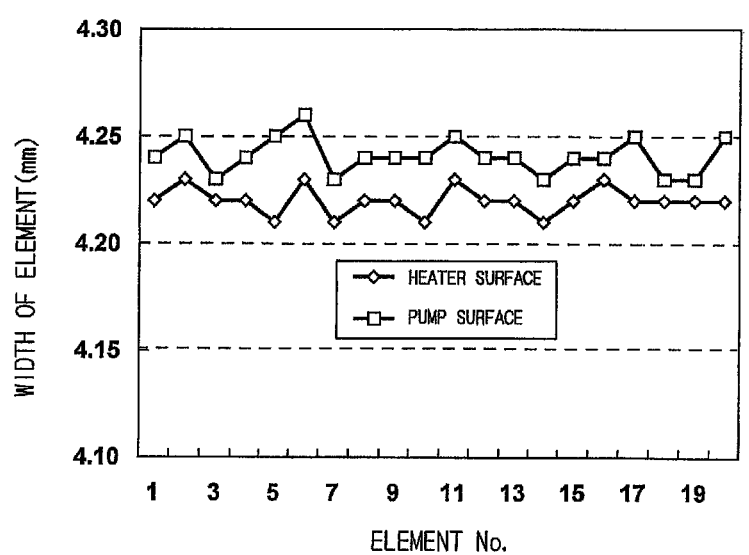
FIG. 12 is a view showing the result of measuring an element width of a heater surface side and a pump surface side of twenty sensor elements.

FIG. 11 is a view showing the result of measuring the degrees of the angles P1 to P4 of twenty sensor elements obtained by burning twenty chips. FIG. 12 is a view showing the result of measuring an element width of a heater surface side and a pump surface side of those twenty sensor elements. The results shown in FIGS. 11 and 12 show that most sensor elements which are obtained have the degrees of the angles P1 and P4 which are acute angles smaller than ninety degrees within a range of one degree, and the degrees of the angles P2 and P3 which are obtuse angles larger than ninety degrees within a range of one degree. It has been thus confirmed that the shape of the chip is mostly maintained even after burning and the outline shape of the sensor element is trapezoid satisfying the equations (1) to (3).

Comparative Example

The sensor element is manufactured similarly to the above inventive example other than cutting the chip at the step 5.

The cutting of chips is performed by previously specifying only the position of the cutting line at the most external side with the cutting marks or the like, determining the cutting positions so as to divide the internal region equally by the number of chips which are to be cut out, and thereafter performing the cutting in the order from the cutting position at the far right.

FIG. 13 is a view showing the result of the amount of misalignment in the horizontal direction between the center position of the vertical cutting mark CM1 and the intersection position of the corresponding actual cutting line CL1 ant cutting line CL2, with respect to the chip according to the comparative example, similarly to the inventive example. The average value of the amount of misalignment in the horizontal direction is 36.9 μm, and the standard deviation is 15.0 μm.

FIG. 14 is a view showing the result of measuring the degrees of the angles P2 and P3, with respect to the chip according to the comparative example obtained by the cutting similarly to the inventive example. The squares show the result of the degree of the angle P2, and the triangles show the result of the degree of the angle P3. FIG. 14 shows the case where the cutting is performed in the order from the side of the element No. 20. As understood from FIG. 14, the chips which are cut in the beginning have larger angular difference, and the chips which are cut in the later phases have smaller angular difference. This is considered that difference of resistance added to the right and left surfaces of the cutting knife in the nonuniform cutting is larger in the initial cutting.

Comparison of Inventive Example and Comparative Example

As has been confirmed from comparing the results shown in FIGS. 9 and 13, the precision of the cutting positions is more enhanced when aligning the cutting positions by specifying the cutting marks in cutting at the respective cutting lines as described in the inventive example.

Also, as has been confirmed from comparing the results shown in FIGS. 10 and 14, the precision of the outline shape (reproducibility) is more superior in the example performing the uniform cutting by priority. This means that the sensor element having the outline shape which is more resistant to breaks and cracks can be obtained more reliably.

While the invention has been shown and described in detail, the foregoing description is in all aspects illustrative and not restrictive. It is therefore understood that numerous modifications and variations can be devised without departing from the scope of the invention.

What is claimed is:

1. A sensor element manufactured by a method comprising the steps of:
    (a) forming a predetermined circuit pattern on each of a plurality of ceramics green sheets;
    (b) forming a laminated body by laminating said plurality of ceramics green sheets on each of which said circuit pattern is formed;
    (c) defining a cutting order of a plurality of cutting positions previously defined for said laminated body, said cutting order being defined such that the cutting position is where a difference of resistance added to both side surfaces of a cutting edge of a cutting component is smallest at the time of cutting with said cutting component;

(d) cutting out a plurality of elements from said laminated body, by cutting said laminated body with said cutting component in accordance with said cutting order; and (e) burning said plurality of elements which are cut out in said step (d), wherein said sensor element comprises a main component which is oxygen ion conductive solid electrolyte and said sensor element has an outline shape that is quadrilateral and extends perpendicular to a longitudinal direction of said sensor element, wherein when corners of said quadrilateral are A, B, C and D, respectively, the quadrilateral ABCD is a trapezoid having sides AD and BC which are substantially parallel to each other, and said corners A, B, C, and D have angles P1, P2, P3 and P4, respectively, which are defined as:

$0°<P2-90°, P3-90°≤1°$, and $0°<90°-P1, 90°-P4≤1°$, and wherein an inlet for introducing a measurement gas into the sensor element is arranged on a longitudinal end face of the sensor element, and wherein the inlet for introducing the measurement gas and an internal space are arranged in the same layer in the sensor element.

2. A sensor element comprising:

a main component which is oxygen ion conductive solid electrolyte; and a surface of said sensor element has an outline shape that is quadrilateral and extends perpendicular to a longitudinal direction of said sensor element, wherein when corners of said quadrilateral are A, B, C and D, respectively, the quadrilateral ABCD is a trapezoid having sides AD and BC which are substantially parallel to each other, said corners A, B, C, and D have angles P1, P2, P3 and P4, respectively, which are defined as:

$0°<P2-90°, P3-90°≤1°$, and $0°<90°-P1, 90°-P4≤1°$, and an inlet for introducing a measurement gas into the sensor element is arranged on a longitudinal end face of the sensor element, and wherein the inlet for introducing the measurement gas and an internal space are arranged in the same layer in the sensor element.

3. The sensor element according to claim 2, further comprising:

a heater for heating said sensor element, which is provided inside said sensor element to be adjacent to a surface of said sensor element, said surface rendering said side BC.

4. A sensor element comprising:

a main component which is oxygen ion conductive solid electrolyte; and a surface of said sensor element has an outline shape that is quadrilateral and extends perpendicular to a longitudinal direction of said sensor element, wherein when corners of said quadrilateral are A, B, C and D, respectively, the middle point of the side BC is M, the intersection of the perpendicular dropped from the middle point M to the side AD is H, sides AD and BC are substantially parallel to each other, $AH≥BM$, $DH≥CM$, and $AD>BC$, and said corners A, B, C, and D have angles P1, P2, P3 and P4, respectively, which are defined as:

$0°<P2-90°, P3-90°≤1°$, and $0°<90°-P1, 90°-P4≤1°$, and an inlet for introducing a measurement gas into the sensor element is arranged on a longitudinal end face of the sensor element, and wherein the inlet for introducing the measurement gas and an internal space are arranged in the same layer in the sensor element.

5. The sensor element according to claim 4, further comprising:

a heater for heating said sensor element, which is provided inside said sensor element to be adjacent to a surface of said sensor element, said surface rendering said side BC.

6. The sensor element according to claim 1, wherein the sensor element further comprises a gas distribution part that is arranged in the sensor element from the inlet along the longitudinal direction of the sensor element.

7. The sensor element according to claim 2, further comprising a gas distribution part that is arranged in the sensor element extending from the inlet along the longitudinal direction of the sensor element.

8. The sensor element according to claim 4, further comprising a gas distribution part that is arranged in the sensor element extending from the inlet along the longitudinal direction of the sensor element.

9. The sensor element according to claim 1, wherein said inlet for introducing the measurement gas is defined by four surfaces.

10. The sensor element according to claim 2, wherein said inlet for introducing the measurement gas is defined by four surfaces.

11. The sensor element according to claim 4, wherein said inlet for introducing the measurement gas is defined by four surfaces.

* * * * *